United States Patent
Park et al.

(10) Patent No.: US 9,550,858 B2
(45) Date of Patent: Jan. 24, 2017

(54) HYDROXYL-CAPPING MONOMER, ITS POLYCARBONATE AND ARTICLE CONTAINING THE SAME

(71) Applicant: LG CHEM, LTD., Seoul (KR)

(72) Inventors: Jung Jun Park, Daejeon (KR); Min Jeong Kim, Daejeon (KR); Hyong Min Bahn, Daejeon (KR); Moo Ho Hong, Daejeon (KR); Young Young Hwang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 151 days.

(21) Appl. No.: 14/412,175

(22) PCT Filed: Jul. 1, 2014

(86) PCT No.: PCT/KR2014/005842
§ 371 (c)(1),
(2) Date: Dec. 30, 2014

(87) PCT Pub. No.: WO2015/002429
PCT Pub. Date: Jan. 8, 2015

(65) Prior Publication Data
US 2016/0272759 A1    Sep. 22, 2016

(30) Foreign Application Priority Data

Jul. 1, 2013 (KR) .................. 10-2013-0076446
Jun. 23, 2014 (KR) .................. 10-2014-0076331

(51) Int. Cl.
| | | |
|---|---|---|
| *C08G 64/00* | (2006.01) | |
| *C08G 64/14* | (2006.01) | |
| *C07C 69/84* | (2006.01) | |
| *C08G 64/16* | (2006.01) | |
| *C07C 69/94* | (2006.01) | |
| *C08G 64/40* | (2006.01) | |
| *C08G 63/02* | (2006.01) | |

(52) U.S. Cl.
CPC ............. *C08G 64/14* (2013.01); *C07C 69/84* (2013.01); *C07C 69/94* (2013.01); *C08G 64/1608* (2013.01); *C08G 64/40* (2013.01); *C08G 2120/00* (2013.01)

(58) Field of Classification Search
CPC ....................................................... C08G 64/14
USPC .................................................. 528/196, 198
See application file for complete search history.

(56) References Cited

U.S. PATENT DOCUMENTS

| | | |
|---|---|---|
| 3,146,269 A | 8/1964 | Braus |
| 4,276,226 A | 6/1981 | Clement |
| 4,330,663 A | 5/1982 | Rosenquist |
| 4,927,903 A | 5/1990 | Schreckenberg et al. |

FOREIGN PATENT DOCUMENTS

| | | |
|---|---|---|
| CN | 101845005 A | 9/2010 |
| JP | 5815529 A | 1/1983 |
| JP | 6011441 A | 1/1985 |
| JP | 200952027 A | 3/2009 |
| KR | 10-2009-0057943 A | 6/2009 |
| WO | 2008108492 A1 | 9/2008 |

OTHER PUBLICATIONS

CN 201010203910 Zhou Dewend et al. Side Substitution of Aromatic ester diphenol, preparation method and preparation method of mesomorphic epoxy monomer; 2014.*
CN 201010203910 Zhou Dewend et al. Side Substitution of Aromatic ester diphenol, preparation method and preparation method of mesomorphic epoxy monomer; 2014—English translation.*
"Terminal Chains as a Tool to Modulate the Properties of Bent-Core Liquid Crystals", Nelida Gimeno et al., Chem. Matter, vol. 21, No. 19, pp. 4620-4630, Sep. 1, 2009.
XP002752123: Chemical Abstracts Service, Columbus Ohio, US; Mochizuki, Hiroaki et al: "Polyarylates with excellent heat resistance and moldability, optical films from them, and displays using them"; retrieved Nov. 12, 2015.

\* cited by examiner

*Primary Examiner* — Terressa Boykin
(74) *Attorney, Agent, or Firm* — Dentons US LLP (57) ABSTRACT

Disclosed are a hydroxy-capping monomer, its polycarbonate and an article including the same. Disclosed is a capping monomer capable of greatly improving mechanical properties and weather resistance when applied to polycarbonate, and polycarbonate containing the same, being prepared at high economic efficiency and having superior mechanical properties and excellent weather resistance.

14 Claims, 2 Drawing Sheets

HYDROXYL-CAPPING MONOMER, ITS POLYCARBONATE AND ARTICLE CONTAINING THE SAME

This application is a 35 USC § 371 National Stage entry of International Application No. PCT/KR2014/005842, filed on Jul. 1, 2014, which claims priority of Korean Application Nos. 10-2013-0076446 filed on Jul. 1, 2013 and 10-2014-0076331 filed Jun. 23, 2014, which are hereby incorporated by reference in their entirety.

TECHNICAL FIELD

The present invention relates to a hydroxy-capping monomer, its polycarbonate and an article containing the same. More specifically, the present invention relates to a capping monomer capable of greatly improving mechanical properties and weather resistance when applied to polycarbonate, polycarbonate which contains the same, is prepared at a high economical efficiency and has superior mechanical properties and excellent weather resistance, and an article containing the same.

BACKGROUND ART

A polycarbonate resin is prepared by condensation polymerization of an aromatic diol monomer such as bisphenol A, or a carbonate precursor such as phosgene, has superior impact strength, dimensional stability, weather resistance, transparency and the like, and is widely utilized in a variety of applications including exterior materials of electronic and electric products, automobile parts, constructional materials and optical parts.

Research in which two aromatic diols having different structures are copolymerized to introduce units having different structures into a main chain of polycarbonate and thereby obtain desired physical properties is underway in order to apply the polycarbonate resin to more various fields.

In particular, addition of a UV stabilizer such as benzotriazole as an additive of the polycarbonate resin was suggested in order to provide a polycarbonate resin having weather resistance. However, the UV stabilizer improves weather resistance of the polycarbonate resin, but disadvantageously deteriorates mechanical properties thereof.

DISCLOSURE

Technical Problem

Therefore, the present invention has been made in view of the above problems, and it is one object of the present invention to provide a capping monomer capable of greatly improving mechanical properties and weather resistance when applied to polycarbonate, polycarbonate which contains the same, is prepared at high economic efficiency and has superior mechanical properties and excellent weather resistance, and an article containing the same.

Technical Solution

In accordance with one aspect of the present invention, provided is a hydroxy-capping monomer represented by the following Formula 1:

[Formula 1]

wherein $R_1$ and $R_2$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, Y represents OH or and a and b each independently represent an integer of 1 to 4.

In addition, in accordance with another aspect of the present invention, provided is polycarbonate polymerized from an aromatic diol monomer, a carbonate precursor and the hydroxy-capping monomer represented by Formula 1.

In addition, in accordance with another aspect of the present invention, provided is an article produced from the polycarbonate.

Advantageous Effects

As apparent from the foregoing, the present invention has an effect such as a capping monomer capable of greatly improving mechanical properties and weather resistance when applied to polycarbonate, and polycarbonate which contains the same, is prepared at high economic efficiency and has superior mechanical properties and excellent weather resistance.

BEST MODE

Hereinafter, the present invention will be described in detail.

The hydroxy-capping monomer according to the present invention is represented by the following Formula 1:

[Formula 1]

wherein $R_1$ and $R_2$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, Y represents OH or and a and b each independently represent an integer of 1 to 4.

As used herein, the term "hydroxy-capping monomer" refers a monomer in which a hydroxybenzoic acid is linked to an aromatic diol compound such as bisphenyl A, unless mentioned otherwise. In particular, the hydroxy-capping monomer may include a monomer capped with hydroxybenzoic acid at one or more of ends of the aromatic diol compound.

The hydroxy-capping monomer having a weight average molecular weight of 100 to 200 g/mol, 100 to 150 g/mol, or 130 to 140 g/mol has the effect of providing superior polymerization reactivity.

The hydroxy-capping monomer having a density of 1.45 to 1.48 g/cm$^3$, 1.45 to 1.47 g/cm$^3$, or 1.45 to 1.46 g/cm$^3$ has the effect of providing superior polymerization reactivity.

The hydroxy-capping monomer having a melting point of 200 to 250° C., 205 to 215° C. or 210 to 215° C. has the effect of providing superior polymerization reactivity.

In another example, $R_1$ and $R_2$ each independently represent hydrogen or a C1-C3 alkyl group. In another example, both $R_1$ and $R_2$ represent hydrogen.

In another example, both $R_1$ and $R_2$ represent hydrogen, and X represents a C1-C3 alkylidene group.

The compound represented by Formula 1 may be used as at least one selected from the group consisting of a comonomer, a modifying agent, an impact reinforcing agent and a UV stabilizer.

The compound represented by Formula 1 may be a monomer used in the preparation of polycarbonate.

The compound represented by Formula 1 is for example prepared by esterification of an aromatic diol compound with hydroxybenzoate such as 4-hydroxybenzoic acid in the presence of an acid or base catalyst.

In a specific example, the compound represented by Formula 1 is a monomer capped with hydroxybenzoic acid at both ends thereof, represented by the following Formula 2.

[Formula 2]

wherein $R_1$ and $R_2$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO— and —SO$_2$—, and a and b are each independently an integer of 1 to 4.

The polycarbonate according to the present invention is polymerized from an aromatic diol monomer, a carbonate precursor, and the hydroxy-capping monomer represented by the following Formula 1:

[Formula 1]

wherein $R_1$ and $R_2$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, Y represents OH or and a and b each independently represent an integer of 1 to 4.

The polycarbonate is for example polymerized using 25 to 85% by weight of the aromatic diol monomer, 1 to 60% by weight of the hydroxy-capping monomer represented by Formula 1, and 10 to 70% by weight of the carbonate precursor, with respect to 100% by weight in total of the aromatic diol monomer, the carbonate precursor and the hydroxy-capping monomer represented by Formula 1. Within this range, there are effects in that intrinsic mechanical properties of polycarbonate are maintained and weather resistance is excellent.

In another example, the polycarbonate is for example polymerized using 30 to 70% by weight of the aromatic diol monomer, 5 to 50% by weight of the hydroxy-capping monomer represented by Formula 1, and 20 to 60% by weight of the carbonate precursor, with respect to 100% by weight in total of the aromatic diol monomer, the carbonate precursor and the hydroxy-capping monomer represented by Formula 1.

The carbonate precursor is for example a compound represented by the following Formula 3:

[Formula 3]

wherein $X_1$ and $X_2$ each independently represent halogen, a haloalkyl group, a halocycloalkyl group, a haloaryl group, an alkoxy group or a haloalkoxy group. In this case, there is an effect of imparting intrinsic properties of polycarbonate.

In another example, the carbonate precursor comprises at least one selected from the group consisting of dimethyl carbonate, diethyl carbonate, dibutyl carbonate, dicyclohexyl carbonate, diphenyl carbonate, ditolyl carbonate, bis(chlorophenyl) carbonate, di-m-cresyl carbonate, di-naphthyl carbonate, bis(diphenyl) carbonate, phosgene, triphosgene, diphosgene, bromophosgene and bishaloformate and is preferably triphosgene or phosgene. In this case, there is an effect of providing intrinsic properties of polycarbonate.

The aromatic diol monomer for example comprises at least one selected from the group consisting of bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl)sulfide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane (bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, 1,1-bis(4-hydroxyphenyl)-1-phenylethane, bis(4-hydroxyphenyl)diphenylmethane, and α,ω-bis[3-(o-hydroxyphenyl)propyl]polydimethylsiloxane, and is preferably bisphenol A. In this case, there is an effect of increasing flowability of polycarbonate.

The hydroxy-capping monomer represented by Formula 1 is for example 0.1 to 99.9 mol %, 1 to 99 mol %, 2 to 50 mol %, or 2 to 10 mol %, based on the content of the aromatic diol compound. Within this range, intrinsic properties of polycarbonate are excellent and side reaction in which the capped monomer of Formula 1 acts as a molecular weight modifier when the capping monomer remains by non-reaction is prevented.

The polycarbonate is for example polymerized further using a molecular weight modifier.

The molecular weight modifier is for example mono-alkylphenol.

The mono-alkylphenol for example comprises at least one selected from the group consisting of p-tert-butylphenol, p-cumylphenol, decylphenol, dodecylphenol, tetradecylphenol, hexadecylphenol, octadecylphenol, eicosylphenol, docosylphenol and triacontylphenol, and is preferably para-tert-butylphenol. In this case, an effect of controlling a molecular weight is great.

The molecular weight modifier is for example present in an amount of 0.01 to 10 parts by weight, 0.1 to 6 parts by weight, or 1 to 5 parts by weight, based on 100 parts by weight in total of the aromatic diol monomer, the carbonate precursor and the hydroxy-capping monomer represented by Formula 1. Within this range, the target molecular weight can be obtained.

The polycarbonate for example has a glass transition temperature of 140 to 180° C., or 140 to 160° C., and a weight average molecular weight of 10,000 to 100,000 g/mol, 20,000 to 80,000 g/mol, or 30,000 to 60,000 g/mol. Within this range, there are effects of maintaining intrinsic mechanical properties of polycarbonate and improving weather resistance thereof.

The polycarbonate for example exhibits a weather resistance providing an aeration time of 1,500 hours or longer, wherein the weather resistance is measured as a Yellowness Index variation (AYI) factor by using a weatherometer in accordance with ASTM D1003. Within this range, there are effects of improving weather resistance and providing superior physical property balance.

The polycarbonate is for example represented by the following Formula 4:

[Formula 4]

wherein $R_1$, $R_2$, $R_3$ and $R_4$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, V represents —O— or a and b each independently represent an integer of 1 to 4, and n and m are integers, with the proviso that 0<n+m≤99.

In another example, n is an integer of 10 to 90, or an integer of 25 to 75, m is an integer of 10 to 90, or an integer of 25 to 75, and n+m is 1 to 99, or 50 to 99. Within this range, there are effects of superior mechanical properties and weather resistance.

The polycarbonate is for example represented by the following Formula 5:

[Formula 5]

wherein $R_1$, $R_2$, $R_3$ and $R_4$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, a and b each independently represent an integer of 1 to 4, and n and m are integers, with the proviso that $0<n+m\leq99$.

Figure 3:
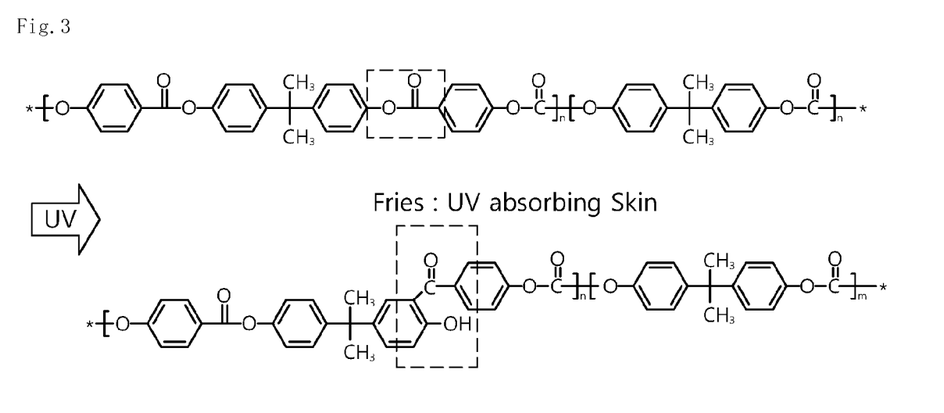
FIG. 3 is a schematic view illustrating a reaction mechanism upon UV irradiation of polycarbonate according to the present invention in Example 1.

The polycarbonate may for example comprise polycarbonate by undergoing rearrangement reaction represented by the following Formula 6 upon UV irradiation:

[Formula 6]

wherein $R_1$, $R_2$, $R_3$ and $R_4$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, a and b each independently represent an integer of 1 to 4, and n and m are integers, with the proviso that $0<n+m\leq99$ (See FIG. 3).

The square area in Formula 6 corresponds to a region considered as a UV absorbing skin parts.

In a specific example, the polycarbonate may comprise polycarbonate represented by the following Formula 7:

A method of preparing the polycarbonate according to the present invention is for example interfacial polymerization.

In this case, there is an effect in that polymerization is possible at an atmospheric pressure and a low temperature, and control of molecular weight is easy.

The interfacial polymerization is for example carried out by reacting a diol monomer, a carbonate precursor and a molecular weight modifier in the presence of an acid binder and an organic solvent.

The interfacial polymerization may for example comprise pre-polymerization, then an addition of a coupling agent and polymerization. In this case, polycarbonate resins with a high molecular weight can be obtained.

There is no particular limitation as to other substances used in the interfacial polymerization so long as they can be used for polymerization of polycarbonate and the amount of used substance may be controlled, as desired.

The acid binder is for example alkali metal hydroxide such as sodium hydroxide or potassium hydroxide, or an amine compound such as pyridine.

The organic solvent is not particularly limited so long as it is commonly used in the polymerization of polycarbonate and is for example halogenated hydrocarbon such as methylene chloride or chlorobenzene.

The interfacial polymerization is for example carried out further using a reaction accelerator for facilitating reaction

[Formula 7]

such as a tertiary amine compound, for example, triethylamine, tetra-n-butylammonium bromide or tetra-n-butylphosphonium bromide, a quaternary ammonium compound, or a quaternary phosphonium compound.

The interfacial polymerization is carried out at a reaction temperature of, for example, 0 to 40° C., and for a reaction time of, for example, 10 minutes to 5 hours. During reaction, pH is for example preferably maintained at 9 or more, or 11 or more. The molecular weight modifier is for example added before, during or after polymerization.

The article according to the present invention comprises the polycarbonate.

The article is for example an injection-molded article.

The article may for example further comprise one or more selected from the group consisting of an antioxidant, a plasticizer, an anti-static agent, a nucleating agent, a flame retardant, a lubricant, an impact reinforcing agent, a fluorescent bleaching agent, a UV absorber, a pigment and a dye.

A method for producing the article for example includes thoroughly mixing the polycarbonate resin with an additive such as antioxidant using a mixer, extrusion-molding the mixture into a pellet in an extruder, and thoroughly drying the pellet, and then injection-molding the pellet using an injection molding machine.

Hereinafter, preferred examples will be provided for better understanding of the present invention. It will be apparent to those skilled in the art that these examples are only provided to illustrate the present invention and various modifications and alterations are possible within the scope and technical spirit of the present invention. Such modifications and alterations fall within the scope of claims included herein.

EXAMPLE

Example 1

<Preparation Hydroxy-Capping Monomer of Formula 1>

Figure 1:
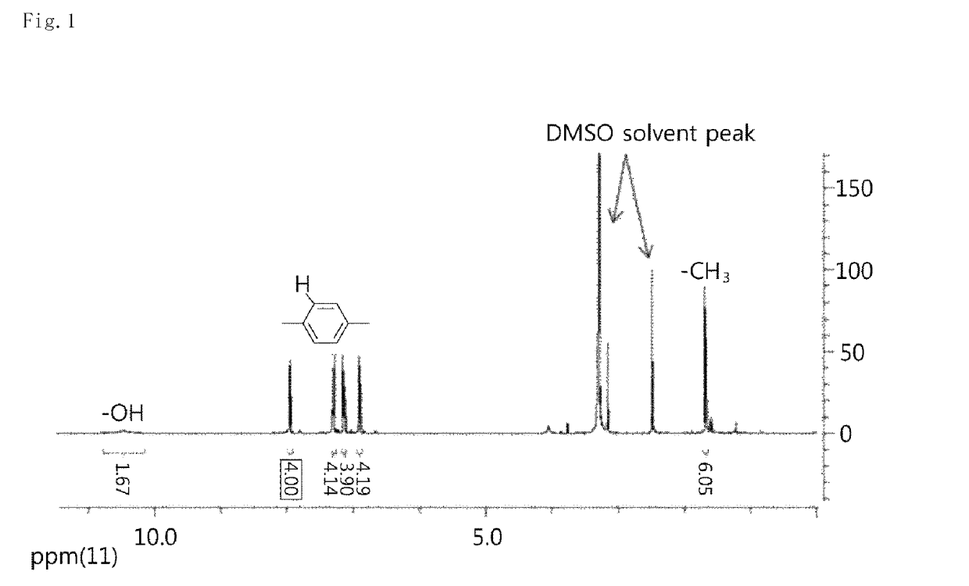
FIG. 1 is a $^1$H NMR spectrum of a hydroxy-capping monomer prepared in Example 1.

382 g (2 eq.) of 4-hydroxybenzoate were slowly added to 287 g (1 eq.) of commercially available bisphenol A (BPA) under basic conditions while purging with nitrogen and reaction proceeded while elevating a reaction temperature from 60° C. to 120° C. After removal of BPA was confirmed by thin layer chromatography (TLC), the reaction was finished by addition of water. The reaction solution was cooled to room temperature, the organic layer was subjected to fractional extraction using ethyl acetate, 1N hydrochloric acid and distilled water, residual moisture present in the organic layer was removed through magnesium sulfate and the residue was filtered to obtain a moisture-free organic layer. The solvent was removed from the obtained organic layer using a vacuum rotary evaporator. The residue was recrystallized using ethyl acetate and methanol to obtain 110 g of a white solid, that is, the compound (HB-BPA) corresponding to Formula 1 (having both ends capped with hydroxy) with a yield of 90% and the structure of the product was observed by $^1$H NMR using Varian 500 MHz (see FIG. 1).

In addition, the obtained product had a weight average molecular weight (Mw) of 138.12 g/mol wherein the weight average molecular weight was measured based on a PC standard using Agilent 1200 series, a density of 1.46 g/cm$^3$ and a melting point of 214.5° C.

<Preparation of Polycarbonate>

Interfacial polymerization was performed by reaction of triphosgene with bisphenol A using HP-BPA of Formula 1 to prepare a polycarbonate copolymer with high weather resistance.

Specifically, 1,159 g of H$_2$O, 143 g of BPA (bisphenol A), 15 g (2 mol % with respect to BPA) of HB-BPA corresponding to Formula 1, 2.8 g of p-tert-butylphenol (PTBP), 100 g of NaOH and 114 g of MeCl$_2$ (MC) were added to a 3 L main reactor equipped with a nitrogen purge device and a condenser and enabling maintenance at room temperature using a circulator, followed by stirring for about 10 to about 20 minutes.

83 g of triphosgene and 114 g of MeCl$_2$ were charged in a 4 L round bottom flask, triphosgene was dissolved therein, and the dissolved triphosgene solution was slowly added to the main reactor containing the BPA solution. After completion of addition, 31 g of triethylamine (TEA) as a coupling agent was added. At this time, a reaction pH was maintained at 11 to 13. After the reaction solution was allowed to stand for 1 hour 20 minutes for sufficient reaction, pH was decreased to 4 by addition of HCl to stop the reaction, TEA was removed, stirring was stopped, the polymer layer was separated from the aqueous layer, the aqueous layer was removed, and the residue was repeatedly washed with pure H$_2$O again, and the above process repeats total 3 to 5 times. After completion of washing, only the polymer layer was extracted, the polymer crystals were obtained by re-precipitation using a non-solvent of methanol, acetone, n-hexane, H$_2$O or the like, and dried at 120° C. The molecular weight of the obtained polycarbonate was measured by GPC using a PC Standard. As a result, it was confirmed that the weight average molecular weight was 33,000 g/mol. (Tg: 147° C.)

Figure 2:
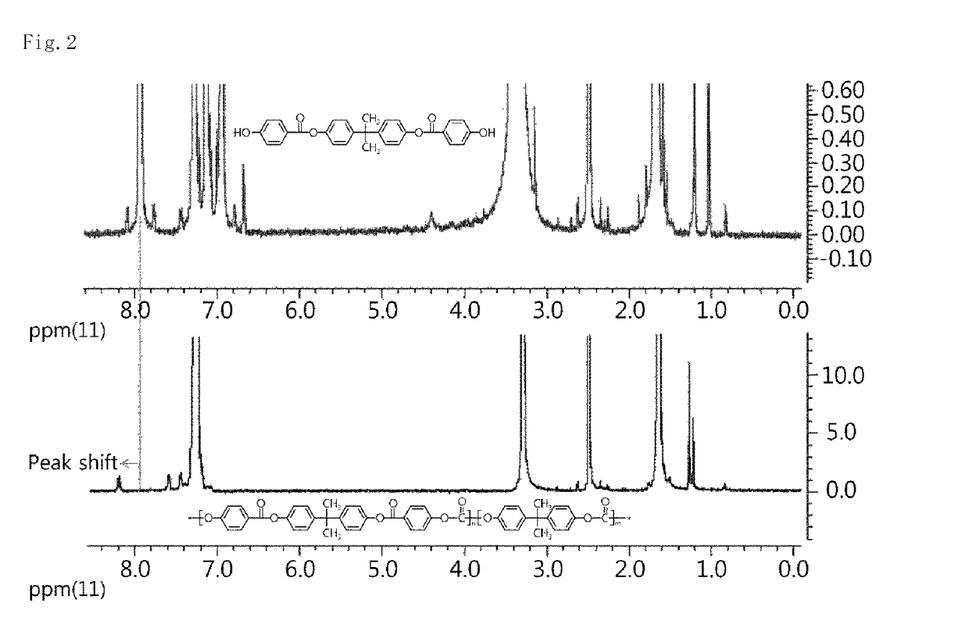
FIG. 2 is a $^1$H NMR spectrum of polycarbonate prepared in Example 1.

In addition, the structure of the produced substance was confirmed by $^1$H NMR using Varian 500 MHz. As a result, it was confirmed that the structure was represented by Formula 4 (see FIG. 2).

<Production of Injection-Molded Sample>

0.050 part by weight of tris(2,4-di-tert-butylphenyl)phosphite and 0.010 part by weight of octadecyl-3-(3,5-di-tert-butyl-4-hydroxyphenyl)propionate were added to the prepared polycarbonate, 0.030 part by weight of pentaerythritol tetrastearate was added thereto, and the resulting mixture was pelletized using a Φ30 mm twin screw extruder provided with a vent, and was injection-molded at a cylinder temperature of 300° C. and a mold temperature of 90° C. using an N-20C injection molding machine produced by JSW Co., Ltd.

Example 2

Polycarbonate and an injection-molded sample thereof were produced in the same manner as in Example 1, except that 5 mol % of HB-BPA was used instead of 2 mol % of HB-BPA in Example 1. The polycarbonate was confirmed to have a weight average molecular weight of 33,000 g/mol (Tg: 147° C.)

Example 3

Polycarbonate and an injection-molded sample thereof were produced in the same manner as in Example 1, except that 10 mol % of HB-BPA was used instead of 2 mol % of HB-BPA in Example 1. The polycarbonate was confirmed to have a weight average molecular weight of 33,000 g/mol (Tg: 147° C.)

Comparative Example 1

Polycarbonate and an injection-molded sample thereof were produced in the same manner as in Example 1, except that bisphenol A (BPA) was further used in the same amount as the HB-BPA used in Example 1, instead of HB-BPA. The polycarbonate was confirmed to have a weight average molecular weight of 33,000 g/mol (Tg: 147° C.)

Comparative Example 2

Polycarbonate and an injection-molded sample thereof were produced in the same manner as in Example 1, except that 20,000 ppm of a conventionally added UV stabilizer product (Tinuvin234) was used instead of 2 mol % of HB-BPA in Example 1. The polycarbonate was confirmed to have a weight average molecular weight of 33,000 g/mol (Tg: 147° C.)

Test Example

Physical properties of the injection-molded samples of polycarbonate produced in Examples 1 to 3 and Comparative Examples 1 to 2 were measured according to the following method. Results are each shown in the following Table 1, FIG. 1, and Table 2.

Weather resistance: variation in Yellowness Index (ΔYI) per elapsed time was measured using a weatherometer in accordance with ASTM D1003.

Room temperature impact strength: measured at 23° C. in accordance with ASTM D256 (⅛ inch, Notched Izod) and recorded.

TABLE 1

|  | Variation in Yellowness Index (ΔYI) per elapsed time (hour) | | | | | | | HB-BPA content (mol %) | Tinuvin 234 (ppm) |
| --- | --- | --- | --- | --- | --- | --- | --- | --- | --- |
|  | 0 | 50 | 100 | 200 | 500 | 1500 | 2000 | | |
| Example 1 | 1.54 | 1.58 | 1.63 | 1.85 | 2.81 | 5.57 | 6.85 | 2 | — |
| Example 2 | 1.82 | 1.83 | 1.86 | 1.96 | 2.61 | 5.21 | 6.11 | 5 | — |
| Example 3 | 2.31 | 2.33 | 2.35 | 2.36 | 2.73 | 4.71 | 5.72 | 10 | — |
| Comparative Example 1 (Neat PC) | 1.36 | 2.27 | 3.21 | 4.61 | 7.09 | 13.29 | 14.39 | — | — |
| Comparative Example 2 | 2.18 | 2.18 | 2.35 | 2.76 | 3.87 | 8.25 | 8.70 | — | 20000 |

As can be seen from Table 1 above, polycarbonate copolymers (Examples 1 to 3) comprising the hydroxybenzoate-capping monomer according to the present invention provided weather resistance of 1,500 hours or longer, while Neat PC (Comparative Example 1) provided weather resistance of 500 hours or longer.

In addition, polycarbonate copolymers (Examples 1 to 3) containing the hydroxybenzoate-capping monomer provided weather resistance of 1,500 hours or longer which was the same as the conventional polycarbonate (Comparative Example 2) in which Tinuvin234 as a UV stabilizer is added to Neat PC.

Figure 4:
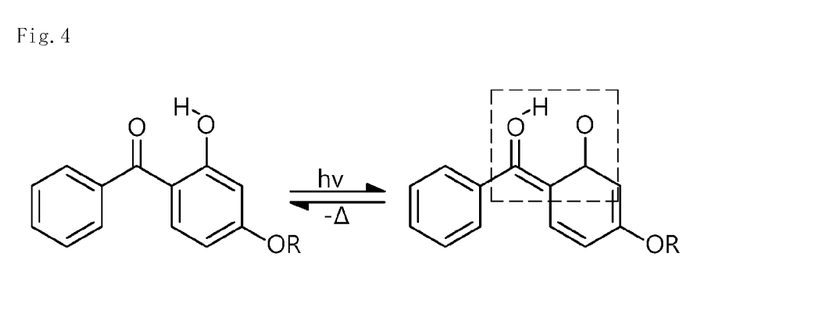
FIG. 4 is a schematic view illustrating a reaction mechanism of providing weather resistance by addition of a UV stabilizer in Comparative Example 2.

When comparing FIG. 3 schematically illustrating a reaction mechanism when UV is emitted to the polycarbonate according to Example 1 with FIG. 4 illustrating UV blocking effect upon addition of Tinuvin234 as a UV stabilizer according to Comparative Example 2, the structure improving weather resistance in FIG. 3 is the same as the structure of the UV stabilizer inducing excited state intramolecular proton transfer in FIG. 4.

TABLE 2

| Items | Notched Izod (23° C.) kgf-m/m |
| --- | --- |
| Example 1 | 82.3 |
| Example 2 | 82.5 |
| Example 3 | 83.1 |
| Comparative Example 1 | 81.2 |
| Comparative Example 2 | 75 |

As can be seen from Table 2 above, polycarbonate copolymers according to the present invention (Examples 1 to 3) exhibited improved room temperature impact strength as compared to Neat PC (Comparative Example 1) or the conventional polycarbonate (Comparative Example 2) in which Tinuvin234 as a UV stabilizer is added to Neat PC.

In addition, it can be seen that room temperature impact strength of Examples 1 to 3 is improved in proportion to a content of the hydroxyl-capping compound of Formula 1 increases.

What is claimed is:

1. Polycarbonate polymerized from an aromatic diol monomer, a carbonate precursor and a hydroxy-capping monomer represented by the following Formula 1:

[Formula 1]

wherein $R_1$ and $R_2$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, Y represents OH or and a and b each independently represent an integer of 1 to 4.

2. The polycarbonate according to claim 1, wherein the polycarbonate is polymerized from 25 to 85% by weight of the aromatic diol monomer, 1 to 60% by weight of the hydroxy-capping monomer represented by Formula 1, and 10 to 70% by weight of the carbonate precursor, with respect to 100% by weight in total of the aromatic diol monomer, the carbonate precursor and the hydroxy-capping monomer represented by Formula 1.

3. The polycarbonate according to claim 1, wherein the hydroxy-capping monomer represented by Formula 1 is present in an amount of 0.1 to 99.9 mol %, based on the content of the aromatic diol compound.

4. The polycarbonate according to claim 2, wherein the polymerization is interfacial polymerization.

5. The polycarbonate according to claim 1, wherein the carbonate precursor is a compound represented by the following Formula 3:

[Formula 3]

wherein $X_1$ and $X_2$ each independently represent halogen, a haloalkyl group, a halocycloalkyl group, a haloaryl group, an alkoxy group or a haloalkoxy group.

6. The polycarbonate according to claim 1, wherein the aromatic diol monomer comprises at least one selected from the group consisting of bis(4-hydroxyphenyl)methane, bis(4-hydroxyphenyl)ether, bis(4-hydroxyphenyl)sulfone, bis(4-hydroxyphenyl)sulfoxide, bis(4-hydroxyphenyl)sulfide, bis(4-hydroxyphenyl)ketone, 1,1-bis(4-hydroxyphenyl)ethane, 2,2-bis(4-hydroxyphenyl)propane (bisphenol A), 2,2-bis(4-hydroxyphenyl)butane, 1,1-bis(4-hydroxyphenyl)cyclohexane (bisphenol Z), 2,2-bis(4-hydroxy-3,5-dibromophenyl)propane, 2,2-bis(4-hydroxy-3,5-dichlorophenyl)propane, 2,2-bis(4-hydroxy-3-bromophenyl)propane, 2,2-bis(4-hydroxy-3-chlorophenyl)propane, 2,2-bis(4-hydroxy-3-methylphenyl)propane, 2,2-bis(4-hydroxy-3,5-dimethylphenyl)propane, 1,1-bis(4-hydroxyphenyl)-1-phenylethane, bis(4-hydroxyphenyl)diphenylmethane, and α,ω-bis[3-(o-hydroxyphenyl)propyl]polydimethylsiloxane.

7. The polycarbonate according to claim 5, wherein the polycarbonate is polymerized further using a molecular weight modifier.

8. The polycarbonate according to claim 7, wherein the molecular weight modifier comprises mono-alkylphenol.

9. The polycarbonate according to claim 4, wherein the molecular weight modifier is present in an amount of 0.01 to 10 parts by weight, based on 100 parts by weight in total of the aromatic diol monomer, the carbonate precursor and the hydroxy-capping monomer represented by Formula 1.

10. The polycarbonate according to claim 1, wherein the polycarbonate has a weight average molecular weight of 10,000 to 100,000 g/mol and a glass transition temperature of 140 to 180° C.

11. The polycarbonate according to claim 1, wherein the polycarbonate is represented by the following Formula 4:

[Formula 4]

wherein $R_1$, $R_2$, $R_3$ and $R_4$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, V represents —O— or a and b each independently represent an integer of 1 to 4, and n and m are integers, with the proviso that 0<n+m≤99.

12. The polycarbonate according to claim 1, wherein the polycarbonate is represented by the following Formula 5:

[Formula 5]

wherein $R_1$, $R_2$, $R_3$ and $R_4$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, a and b each independently represent an integer of 1 to 4, and n and m are integers, with the proviso that 0<n+m≤99.

13. The polycarbonate according to claim 1, wherein the polycarbonate comprises polycarbonate represented by the following Formula 6 upon UV irradiation:

[Formula 6]

wherein $R_1$, $R_2$, $R_3$ and $R_4$ each independently represent hydrogen or a C1-C12 alkyl group, X is selected from a C1-C12 alkyl group, a C3-C14 cycloalkyl group, a C1-C12 alkylidene group, a C3-C14 cycloalkylidene group, a C6-C12 aryl group, a C7-C13 arylalkyl group, a C6-C18 arylene group, —O—, —S—, —CO—, and —SO$_2$—, a and b each independently represent an integer of 1 to 4, and n and m are integers, with the proviso that 0<n+m≤99.

14. An article comprising the polycarbonate according to claim 1.

\* \* \* \* \*